United States Patent [19]

Corpart et al.

[11] Patent Number: 5,798,421
[45] Date of Patent: Aug. 25, 1998

[54] WATER-SOLUBLE ASSOCIATIVE TRIBLOCK COPOLYMERS

[75] Inventors: Jean-Marc Corpart, Sannois; Bernard Boutevin, Montpellier; Christian Collete, Paris; Raphaelle Ciampa, Istres, all of France

[73] Assignee: Elf Atochem S.A., France

[21] Appl. No.: 728,051

[22] Filed: Oct. 9, 1996

[30] Foreign Application Priority Data

Oct. 9, 1995 [FR] France .................. 95 11849

[51] Int. Cl.[6] .................. C08F 293/00; C08F 4/04
[52] U.S. Cl. .................. 525/326.9; 525/280; 525/328.2; 525/329.1; 525/329.5; 525/350; 525/359.3; 525/376
[58] Field of Search .................. 525/328.2, 329.1, 525/326.9, 329.5, 350, 359.3, 376, 280

[56] References Cited

U.S. PATENT DOCUMENTS

| | | | |
|---|---|---|---|
| 4,130,517 | 12/1978 | Lundberg et al. | 524/606 |
| 5,368,744 | 11/1994 | Wood et al. | 210/734 |

FOREIGN PATENT DOCUMENTS

| | | |
|---|---|---|
| A-80276 | 1/1983 | European Pat. Off. . |
| A-522675 | 1/1993 | European Pat. Off. . |
| 2392963 | 12/1978 | France . |
| 1024172 | 3/1966 | United Kingdom . |

*Primary Examiner*—Irina S. Zemel
*Attorney, Agent, or Firm*—Bell, Boyd & Lloyd

[57] ABSTRACT

This invention relates to copolymers of molecular mass of between 5,000 and 300,000, consisting of a hydrophilic central portion, for example a polyacrylamide chain, and of hydrophobic ends the hydrophobicity of which is comparable with that of alkyl groups containing 4–20 carbons. They are produced by polymerization of hydrophilic monomers with the aid of initiators, for example of azo type, the hydrophobic residues of which will constitute the hydrophobic ends of the final copolymer.

These copolymers are useful for rheological control of aqueous and/or pigmented compositions, like paints.

11 Claims, No Drawings

WATER-SOLUBLE ASSOCIATIVE TRIBLOCK COPOLYMERS

FIELD OF THE INVENTION

The present invention relates to new water-soluble polymers intended to increase the viscosity of aqueous media. It is well known, in fact, that the viscosity of an aqueous medium is increased by the addition of a water-soluble polymer. Such polymers have varied structures which include polyacrylamides, optionally partially hydrolyzed, sodium polyacrylates or sodium polymethacrylates and their copolymers, cellulose derivatives like carboxymethyl cellulose, hydroxyethyl cellulose and methyl cellulose and polysaccharides. They are employed as thickening agents in fields as varied as paints, inks, glues and adhesives, building, cosmetics and pharmacology.

BACKGROUND OF THE INVENTION

However, the use of these conventional water-soluble polymers suffers from serious limitations. In particular, polymers of high molecular mass are employed to obtain good thickening properties. The majority of the industrial applications mentioned require the aqueous solution including the water-soluble polymer to be subjected to a high shear gradient. Such shearing often causes mechanical degradation of the polymer and thus brings about a reduction in the viscosity of the aqueous phase. Although conventional water-soluble polymers of lower molecular mass are less sensitive to degradation under shear, they must be employed in substantially higher concentrations to reach the required viscosity level, and the system is then no longer economically advantageous. Natural products like cellulose derivatives are, furthermore, sensitive to microbial attack and they require the addition of antimicrobial agents. Finally, ionic polymers like, for example, sodium polyacrylates, show good thickening properties in pure water, but these can be rapidly degraded in the presence of salts, and this is often incompatible with many industrial applications.

To improve the performance of water-soluble polymers, associative polymers have been developed which, according to the definition thereof which is given in the Encyclopedia of Polymer Science and Engineering, 2nd edition, 17, 772–779, are water-soluble polymers containing nonpolar groups which assemble into aggregates in polar media. They consist of a backbone comprising predominantly units of a hydrophilic nature and a minority of hydrophobic sequences. When such structures are placed in aqueous solution, their hydrophobic poles undergo association, in order to limit the interactions between water and hydrophobic sequences. The formation of such physical crosslinking nodes can result in the creation of a real network. The physical gel thus formed considerably increases the viscosity of the water. In the case of a filled and/or pigmented aqueous composition, associative polymers also act by creating various bonds between themselves and some constituents of the compositions, probably by giving rise to hydrophobic interactions. They then impart to the filled and/or pigmented compositions to which they are added a less pseudoplastic Theological behaviour which thus facilitates the applications. The aqueous and/or pigmented compositions with which a person skilled in the art frequently has to do, in particular aqueous paints, consist of a liquid phase which may be water or a mixture of water with a water-miscible organic solvent, of a polymer dispersed in the liquid phase, commonly called a "binder", of fillers and/or pigments, of a dispersing agent for the fillers and/or pigments, which may be a water-soluble polymer, and of various adjuvants such as coalescence agents, biocides, foam-suppressors or others and, finally, of a viscosity-increasing (or thickening) agent, which is a natural or synthetic polymer.

In particular, in the case of some paints, a person skilled in the art seeks to obtain compositions whose low-shear viscosity is low enough for the film deposited on the support to be protected to tend to level out satisfactorily the irregularities of thickness which are due to the application, and whose high-shear viscosity is sufficiently high to improve covering power and to reduce splashes when the paints are applied with a roller. The known associative polymers capable of imparting these characteristics include polyurethane associative thickeners and acrylic associative thickeners.

Polyurethane associative agents are polymers of essentially triblock structure, that is to say molecules consisting of three separate portions, the polymerized hydrophilic central portion and two hydrophobic ends, identical or otherwise. The central hydrophilic portion consists of a number of polyether, generally polyethylene oxide, chains. The end portions consist of hydrophobic groups such as, for example, alkyl, aryl or alkylaryl groups. Polyurethane associative polymers are obtained by condensation chemistry. Such agents are described in many patents, as, for example, in patents U.S. Pat. No. 3,770,684, U.S. Pat. No. 4,079,028 and U.S. Pat. No. 4,155,892.

Acrylic associative agents have a different structure, that of a hydrophilic chain along which pendent hydrophobic units are distributed randomly. They are obtained by copolymerization of a functional monomer of the ethylenic carboxylic acids type, optionally esters of these acids and/or other monomers carrying hydrophilic groups, and of ethylenic monomers carrying a hydrophobic side chain, for example a polyether chain like a polyethylene oxide, comprising a hydrocarbon hydrophobic end radical. Acrylic associative polymers are thus encountered in which the functional monomer is a surfactant alcohol acrylate or methacrylate (patents EP 0,013,836 and U.S. Pat. No. 4,384, 096), an oxyethylenated ester of crotonic acid (U.S. Pat. No. 4,569,965), a half-ester of maleic anhydride (patent EP 0,248,621) or a surfactant ether of allyl alcohol (patent EP 0,216,479) or else the result of the condensation of a surfactant alcohol and of an isocyanate containing ethylenic unsaturation (patents U.S. Pat. No. 4,514,552, U.S. Pat. No. 4,600,761 and EP 0,350,414). All these acrylic associative polymers are obtained by radical polymerization.

Although these agents impart the desirable Theological characteristics to the aqueous solutions and compositions in which they are used, they exhibit disadvantages which are awkward for the user. Associative polyurethanes are generally obtained in the form of powder whose aqueous solutions are generally highly viscous and not easy to handle. In addition, in order to produce them it is often necessary to use a cosolvent the presence of which is not desired within the filled and/or pigmented compositions in the formulation of which the associative polymers are involved. Associative polyacrylics, for their part, are water-soluble and thickening only in alkaline media, generally at pH values higher than or equal to 8, and this unfortunately restricts their field of use.

DESCRIPTION OF THE INVENTION

Applicant has now found and developed new water-soluble associative thickening polymers which effectively increase the viscosity of aqueous solutions and provide good Theological control of filled and/or pigmented aqueous compositions in which they are incorporated, the structure of which is of the triblock type, like that of the polyurethanes referred to above, but with a central hydrophilic portion resulting from the radical polymerization of water-soluble unsaturated monomers, and identical or nonidentical hydrophobic ends. The constituent monomers in this central hydrophilic chain are water-soluble unsaturated monomers taken from the group consisting of acrylamide and its N-substituted derivatives like 2-acrylamido-2-methylpropanesulphonic acid (AMPS), N-(dimethylamino)methylacrylamide, N-(trimethylammonium)methylacrylamide chloride, acrylic acid, its salts and its aminoalkyl esters like N,N-dimethylaminoethyl acrylate, and N-vinyl-2-pyrrolidone.

These triblock polymers are obtained by a radical polymerization process which includes an initiation stage during which the decomposition of an initiator containing hydrophobic chain units produces two primary radicals containing a hydrophobic chain. Next, during the propagation stage, these primary radicals add a number of monomers, resulting in the appearance in the mixture of growing macroradicals which have a hydrophobic end and a reactive polymerized portion which either can, in its turn, add other monomers or else which undergoes the termination stage. The termination may take place either by disproportionation between two macroradicals, resulting in two diblock polymers, each made up of a polymerized portion and of a hydrophobic radical, or by recombination of two macroradicals, resulting in a single, triblock, polymer made up of a polymerized hydrophilic central portion and two hydrophobic ends, or, finally, by recombination of a macroradical with a primary radical originating from the initiator, also resulting in a triblock polymer of comparable structure. In order to obtain oligomers or polymers according to the invention, that is to say compounds of essentially triblock structure, it is necessary to adopt polymerization conditions in which the termination process takes place predominantly by recombination. This is achieved, on the one hand, by employing a large quantity of initiator in order to promote recombination with primary radicals and, on the other hand, by using acrylic monomers from the group selected above. Acrylamide and its derivatives and acrylic acid and its esters constitute an advantageous choice for this purpose. Methacrylic monomers like methacrylic acid and its esters, as well as methacrylamide and its N-substituted derivatives which largely give rise to termination by disproportionation, cannot be employed alone within the scope of the invention. They can, nevertheless, be employed in large quantities which it is appropriate, however, to restrict to 80%, in combination with acrylic acid and its derivatives or acrylamide and its derivatives, in order to make copolymers according to the invention, the latter rapidly imposing on the system their mechanism of termination by recombination of macroradicals.

Vinyl acetate, which is not a water-soluble monomer, can also be employed. In this case the polymerization is followed by a hydrolysis which converts the resulting polyvinyl acetate to water-soluble polyvinyl alcohol.

The initiators with hydrophobic chain units according to the invention comprise in their structure at least one reactive functional group conventionally employed for generating radicals, like azo, peroxide or perester functional groups. Preference is given to azo and perester initiators.

The perester initiators containing hydrophobic units which can be employed within the scope of the invention correspond to the following general formulae:

R—C(O)—O—O—C(O)—R    (Ia)

R—C(O)—O—O—R'    (Ib)

in which R and R' are organic hydrophobic radicals taken from the group consisting of alkyl or cycloalkyl hydrocarbon aliphatic groups containing from 4 to 20 carbons, aromatic polynuclear groups, alkylaryl groups and polyalkylene oxide groups where the alkylene is propylene or a higher homologue, with at least one alkylene unit per hydrophobic segment R or R'. R and R' may contain, at least partly, fluorine-containing groups. Such fluorine-containing groups have, for example, the following structures:

$C_nF_{2n+1}$—$(CH_2)_m$— with n and m such that $2 \leq n \leq 16$ and $0 \leq m \leq 11$, or $C_nF_{2n+1}O$—$(CF(CF_3)CF_2O)_a$—$CF(CF_3)$— with n and a such that $2 \leq n \leq 16$ and $0 \leq a \leq 3$.

The preparation of the perester initiators containing fluorine-containing groups is described in the literature, for example in patents EP 405396, JP 50 97797, JP 51 70731, and in the paper by H. Sawada, "Fluorinated Organic Peroxides—Their Decomposition Behaviour and Applications", Reviews on Heteroatom Chemistry, volume 8, p. 205 (1993).

The preparation of perester initiators containing hydrocarbon hydrophobic groups is described, for example, in patents DE 16 43599, DE 17 68199 and DE 29 28020.

Azo initiators containing hydrophobic units which can be employed within the scope of the invention correspond to the following general formula:

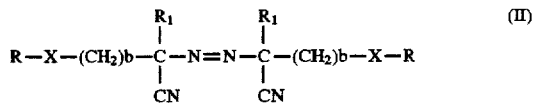

$$R-X-(CH_2)b-\underset{\underset{CN}{|}}{\overset{\overset{R_1}{|}}{C}}-N=N-\underset{\underset{CN}{|}}{\overset{\overset{R_1}{|}}{C}}-(CH_2)b-X-R \qquad (II)$$

in which R has the same meaning as in formulae (Ia) and (Ib); X denotes a divalent group like, for example, CO, COO, OCO, $SO_2$, an oxygen atom or a sulphur atom; X can also denote a direct bond (in other words X is absent as a group); b is an integer ranging from 0 to 11; and $R_1$ denotes an alkyl group containing from 1 to 4 carbon atoms. As in the case of formulae (Ia) and Ib), R may comprise, at least partially, fluorine-containing groups.

The azo initiators containing hydrophobic units may also have the following chemical formula:

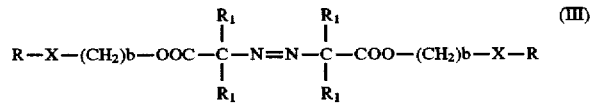

$$R-X-(CH_2)b-OOC-\underset{\underset{R_1}{|}}{\overset{\overset{R_1}{|}}{C}}-N=N-\underset{\underset{R_1}{|}}{\overset{\overset{R_1}{|}}{C}}-COO-(CH_2)b-X-R \qquad (III)$$

where X, b, R and $R_1$ have the same meaning as above.

Another possible structure of the azo initiators containing hydrophobic units is the following:

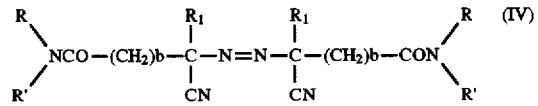

$$\underset{R'}{\overset{R}{\diagdown}}N-CO-(CH_2)b-\underset{\underset{CN}{|}}{\overset{\overset{R_1}{|}}{C}}-N=N-\underset{\underset{CN}{|}}{\overset{\overset{R_1}{|}}{C}}-(CH_2)b-CO-N\underset{R'}{\overset{R}{\diagup}} \qquad (IV)$$

where b, R and $R_1$ have the same meaning as above and R' is a hydrogen atom or has the same meaning as R.

The preparation of such azo initiators is sparsely described in the literature. There is, for example, the description of an initiator of the type (IV) in the paper by H. Kitano et al. (Macromolecules, 1991, 24, 42–46) with b=2, $R_1$=$CH_3$ and R=R'=$C_{18}H_{37}$. Similarly, O. Loubet has synthesized azo initiators in which the hydrophobic portions are fluorinated (J. M. Bessiere, B. Boutevin, O. Louvet, Eur. Polym. J., 1995, vol. 31, No. 6, 573–580).

The polymers of the present invention are prepared by following the techniques, well known per se, of polymerization of monomer(s) in a solvent or a mixture of solvents, it being possible for the total concentration of the monomer (s) to vary between 1 and 20% by-weight and preferably between 5 and 10%. The solvents which at the same time dissolve the hydrophilic monomer(s) and the initiator containing hydrophobic units can be employed. In general, alcohols (for example methanol), ketones (for example acetone or methyl ethyl ketone), ethers (for example tetrahydrofuran) and nitrile-containing solvents (for example acetonitrile or butyronitrile) can be employed. The preferred solvents of those which have low transfer constants ($<10^{-2}$), as, for example, acetonitriles.

The monomers are dissolved in the solvent with stirring and placed under inert atmosphere (for example nitrogen) and the solution is then heated to the polymerization temperature. The initiator, generally predissolved in a small quantity of solvent, is next added to the solution. Another method of polymerization that can be employed in the invention is to place only a portion of the monomer(s) in solution in the reactor and to run the other portion in during the polymerization.

The polymer formed during the polymerization reaction precipitates most of the time in the reaction mixture and is recovered simply by filtration in the form of a solid. In some cases the precipitation is not straightforward, the reaction mixture simply becomes milky and the polymer is then recovered by precipitation in a nonsolvent.

The quantity of initiator containing hydrophobic units which is added to the reaction mixture depends on the synthesis conditions which are adopted (especially the temperature) and on the molecular masses of the polymers which it is intended to obtain. It can vary between 0.01 and 15 mol%, relative to the quantity of monomer(s), and preferably from 0.1 to 2.0%.

The reaction temperature may vary within wide limits, that is to say between the ambient temperature and the boiling point of the reaction mixture. The operation is preferably carried out at between 40° and 100° C.

The publications cited which employ difunctional initiators containing hydrophobic units provide an answer solely to the problem of the synthesis of oligomers with small number masses lower than 15,000. The polymers claimed in the present invention have generally higher number molecular masses, of between 5,000 and 300,000 and preferably between 20,000 and 150,000.

EXAMPLES

The following examples illustrate the invention without limiting it.

Example 1: synthesis of a hydrocarbon hydrophobic azo initiator

In a 1-liter three-necked round bottom flask supporting a mechanical stirrer motor, a dropping funnel and a thermometer, a solution containing 24.1 g of 4,4'-azobis(4-cyanopentanoic) acid (Aa), and 47.8 g of octadecanol in 350 ml of tetrahydrofuran is cooled to a temperature of 5° C. A solution consisting of 1.08 g of dimethylaminopyridine and of 37.1 g of dicyclohexylcarbodiimide in 50 ml of tetrahydrofuran is added gradually over 2 hours to the mixture, with the dropping funnel. The reaction mixture is kept stirred for 2 hours more. The dicyclohexyl urea formed precipitates during the reaction and is recovered by filtration. The reaction mixture is then concentrated by evaporation and 150 ml of methanol are added to it. The azo initiator formed precipitates when cold from the tetrahydrofuran/methanol mixture. The reaction yield is of the order of 75%. The structure of the initiator ($A_1$) is established by proton NMR, infrared, DSC and elemental analysis. It corresponds to the formula of the new compound:

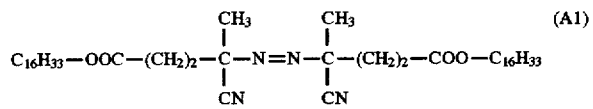

Example 2: synthesis of hydrocarbon associative polyacrylamides 35.5 g (i.e. 0.5 mol) of acrylamide are dissolved in 420 ml of acetonitrile in a 1-liter reactor supporting a condenser, a nitrogen inlet, a mechanical stirrer motor and a temperature probe. The reaction mixture is heated to a temperature of 80° C. under nitrogen circulation. 1.82 g of initiator ($A_1$) diluted in 40 ml of acetonitrile, i.e. 0.5 mol% relative to the quantity of acrylamide, are then added. A white precipitate forms rapidly. The reaction mixture is kept at 80° C. for 30 minutes, until the end of the polymerization. The polymer ($P_{1H}$) formed is recovered by filtration, washed with acetonitrile and with acetone and then dried.

In the same conditions polymerizations are carried out with variable quantities of initiator, i.e. 0.75 mol% (2.73 g) or 1.0 mol% (3.64 g) of ($A_1$) relative to the acrylamide. The polymers ($P_{2H}$) and ($P_{3H}$) are obtained, respectively.

Example 3: synthesis of a fluorine-containing hydrophobic azo initiator

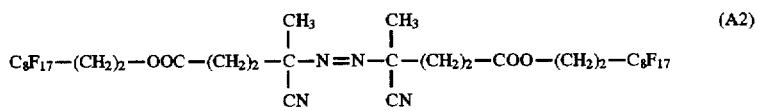

In a 1-liter three-necked round bottom flask supporting a mechanical stirrer motor, a dropping funnel and a thermometer a solution consisting of 11.18 g of 4,4'-azobis(4-cyanopentanoic) acid (Aa) and of fluoro alcohol, $C_8F_{17}$—$(CH_2)_2$—OH in 350 ml of tetrahydrofuran is cooled to a temperature of 5° C. A solution including 0.5 g of dimethylaminopyridine and 19.02 g of dicyclohexylcarbodiimide in 50 ml of tetrahydrofuran is added gradually over 2 hours to the mixture, with the dropping funnel. The reaction mixture is kept stirred for 2 hours more. Dicyclohexyl urea precipitates during the reaction and is recovered by filtration. The fluoro azo initiator formed is in the form of two isomers whose solubility properties are different in tetrahydrofuran. The first isomer precipitates in the reaction mixture at the same time as dicyclohexyl urea. Being of no value for the purpose of the invention, it is simply filtered off. The reaction mixture is then concentrated by evaporation and 150 ml of methanol are added to it. The second isomer formed precipitates when cold in the tetrahydrofuran/methanol mixture. The reaction yield of the useful second isomer is of the order of 53%. The structure of this isomer is checked by proton NMR, infrared, DSC and elemental analysis. It corresponds to the expected product, i.e.:

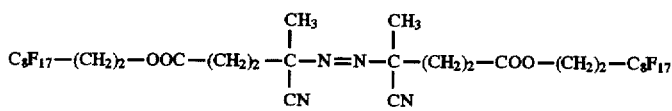

Only this second monomer, soluble in tetrahydrofuran, is employed under reference (A$_2$).

Example 4: synthesis of fluorine-containing associative polyacrylamides

The synthesis of the polymers (P$_{1F}$), (P$_{2F}$) and (P$_{3F}$) is carried out in the same conditions as those employed for the hydrogenated polymers (P$_{1H}$), (P$_{2H}$) and (P$_{3H}$) prepared in Example 2, but employing the initiator (A$_2$). The initiator proportions employed are listed together in the table below:

|  | P$_{1F}$ | P$_{2F}$ | P$_{3F}$ |
| --- | --- | --- | --- |
| mol % of A2 relative to acrylamide | 0.50 | 0.75 | 1.00 |

The fluoro polymers, (P$_{1F}$), (P$_{2F}$) and (P$_{3F}$) are recovered, washed and dried at the end of the reaction in the same way as their hydrogen homologues.

Example 5: synthesis of nonassociative polyacrylamides 35.5 g (i.e. 0.5 mol) of acrylamide are dissolved in 420 ml of acetonitrile in a one-liter reactor; the latter supporting a condenser, a nitrogen inlet, a mechanical stirrer motor and a temperature probe. The reaction mixture is heated to 80° C. under nitrogen circulation. At this temperature 0.7 g of the initiator (Aa) diluted in 40 ml of acetonitrile, i.e. 0.5 mol% relative to the quantity of acrylamide, are added to the solution. A white precipitate forms rapidly. The reaction mixture is then kept at 80° C. for 40 minutes, until the end of the polymerization. The polymer (Pb) obtained is recovered by filtration, washed with acetonitrile and with acetone and then dried.

In the same conditions polymerizations are carried out by introducing into the reaction mixture 0.25 mol% (i.e. 0.35 g) or 0.75 mol% (i.e. 1.05 g) or 1.0 mol% (i.e. 1.40 g) of (Aa) relative to the acrylamide. The polymers (Pa), (Pc) and (Pd) are thus obtained, respectively.

The molecular masses of the polymers, determined by static light scattering in formamide, are listed together in the table below.

|  | Pa | Pb | Pc | Pd |
| --- | --- | --- | --- | --- |
| % Aa | 0.25% | 0.50% | 0.75% | 1.00% |
| molecular mass (M$_w$) | 225 000 | 164 000 | 126 000 | 115 000 |

The polymers synthesized in this example do not comprise any hydrophobic segments at chain ends.

Example 6: rheology of aqueous solutions of the nonassociative and associative polyacrylamides The polymers (P$_{1H}$), (P$_{2H}$), (P$_{3H}$) and (P$_{1F}$), (P$_{2F}$) and (P$_{3F}$) described in Examples 2 and 4 are dissolved in distilled water in a concentration of 8% (g/cm$^3$), while stirred with a bar magnet, for 12 hours. The polymer solutions are left to stand for 6 hours until air bubbles have completely disappeared.

By way of comparison, polyacrylamides (Pa), (Pb), (Pc) and (Pd) are dissolved in water in the same way. These polymers do not comprise any hydrophobic segments at chain ends.

The viscosity of the various solutions is measured with a Carrimed CSL 100 viscometer at a temperature of 20° C.

The following tables show together the viscosities obtained by extrapolation to zero rate gradient.

| polymer |  |  |  |  |  |  |
| --- | --- | --- | --- | --- | --- | --- |
|  | Pa | Pb | Pc | Pd |  |  |
| viscosity: (Pa s) | 0.040 | 0.030 | 0.025 | 0.020 |  |  |
|  | P$_{1F}$ | P$_{2F}$ | P$_{3F}$ | P$_{1H}$ | P$_{2H}$ | P$_{3H}$ |
| viscosity: (Pa s) | 7.5 | 15 | 12.5 | 55 | 25 | 75 |

The results obtained show the thickening nature of the polymers synthesized in accordance with the invention and confirm that triblock structures are obtained. The presence of the hydrophobic segments at the ends of the polymers allows an associative behaviour with the creation of a three-dimensional network in solution, which is responsible for the increase in viscosity.

Example 7: synthesis of a polyacrylamide by telomerization and comparison of rheology with a polymer in accordance with the invention 10 g (i.e. 0.15 mol) of acrylamide are dissolved in 250 ml of acetonitrile and 0.05 g of fluoro thiol C$_8$F$_{17}$—C$_2$H$_4$—SH, i.e. 1 mol% relative to the acrylamide, are then added. The solution is placed in a 500-ml reactor; the latter supporting a condenser, a nitrogen inlet, a mechanical stirrer motor and a temperature probe. The reaction mixture is heated to 80° C. under nitrogen atmosphere. At 80° C. 0.04 g of azoisobutyronitrile are added to the solution. A white precipitate forms rapidly. The reaction is stopped 10 minutes after the addition of the initiator to the mixture.

The structure of the telomer obtained (T1) is checked by proton NMR, infrared and elemental analysis. It corresponds to the following product:

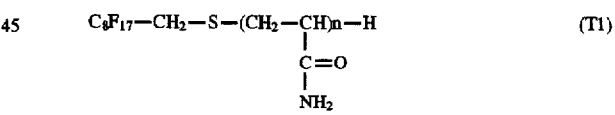

The rheological behaviour of the telomer (T1) is then compared with that of the polymer (P$_{3F}$).

The viscosity measurements (see table which follows), carried out in the same conditions as in Example 6, show that the triblock structure of the polymer (P$_{3F}$) endows it with associative properties which justify its use as a thickener. On the other hand, the telomer (T$_1$), of purely diblock structure, does not permit a thickening of the aqueous solution.

| polymer | P$_{3F}$ | T$_1$ |
| --- | --- | --- |
| viscosity (Pa s) | 12.5 | 0.055 |

Example 8: syntheses with acrylic acid and rheology

In the same operating conditions as in Example 2, a polyacrylic acid (P$_{4H}$) is synthesized by employing 36 g of acrylic acid and 2.73 g of initiator (A$_1$) (i.e. 0.75 mol% relative to the acrylic acid).

Similarly, a polyacrylic acid (Pe) is prepared by employing 36 g of acrylic acid and 1.05 g of initiator (Aa) (i.e. 0.75 mol% relative to the acrylic acid).

A study of the rheological behaviour of the polymers is carried out in the same conditions as in Example 5, the pH of the solutions being fixed at 8. The following table lists together the results obtained:

| polymer | Pe | P$_{4H}$ |
|---|---|---|
| viscosity (Pa s) | 0.4 | 20 |

As in the case of polyacrylamide, a polyacrylic acid synthesized with an initiator containing a hydrophobic segment has the typical behaviour of an associative polymer when it is in solution in water.

Example 9: syntheses with methacrylic acid and rheology

In the same operating conditions as in Example 4 a polymethacrylic acid (P$_{4F}$) is synthesized by employing 43 g of methacrylic acid and 2.93 g of initiator (A$_2$) (i.e. 0.5 mol% relative to the methacrylic acid).

Similarly, a polymethacrylic acid (Pf) is prepared by employing 43 g of methacrylic acid and 0.7 g of initiator (Aa) (i.e. 0.5 mol% relative to the methacrylic acid).

A study of the rheological behaviour of the polymers is carried out in the same conditions as in Example 5, the pH of the solutions being fixed at 8. The following table lists together the results obtained:

| polymer | Pf | P$_{4F}$ |
|---|---|---|
| viscosity (Pa s) | 0.4 | 0.3 |

In contrast to the case of polyacrylamide and of polyacrylic acid, a polymethacrylic acid synthesized with an initiator containing a hydrophobic segment does not show any associative behaviour when it is in solution in water. The structure of the synthesized polymer is essentially diblock.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Water-soluble thickening polymers, of number molecular masses of between 5,000 and 300,000, comprising a central hydrophilic portion resulting from the radical polymerization of water-soluble unsaturated monomers and two hydrophobic, non-polymeric, identical or nonidentical, radicals, the hydrophilic central portion being a chain made up of a sequence of ethylenic hydrophilic monomer residues selected from the group consisting of acrylamide and its N-substituted compounds, acrylic acid, its salts and its aminoalkyl esters.

2. Water-soluble thickening polymers according to claim 1, wherein the central hydrophilic portion is a chain made up of a sequence of acrylamide residues.

3. Water-soluble thickening polymers according to claim 1, wherein in the production of the central hydrophilic portion of which a quantity at most equal to 80% of methacrylic acid, of its esters, of methacrylamide or of its N-substituted compounds has been employed in combination with ethylenic hydrophilic monomers.

4. Water-soluble thickening polymers according to claim 1, wherein their hydrophobic, non-polymeric radicals are R—C(O)— or R'—O—groups in which R and R' are organic hydrophobic radicals selected from the group consisting of alkyl or cycloalkyl hydrocarbon aliphatic groups containing from 4 to 20 carbons, aromatic polynuclear groups, alkylaryl groups and polyalkylene oxide groups where the alkylene is propylene or a higher homologue, with at lease one alkylene unit per hydrophobic segment R or R'.

5. Water-soluble thickening polymers according to claim 4, wherein the radical R is a fluorine-containing group whose structure is $C_nF_{2n+1}$—$(CH_2)_m$—with n and m such that $2 \leq n \leq 16$ and $0 \leq m \leq 11$.

6. Water-soluble thickening polymers according to claim 4, wherein the radial R is a fluorine-containing group whose structure is $C_nF_{2n+1}$O—$(CF(CF_3)CF_2O)_a$—$CF(CF_3)$—with n and a such that $2 \leq n \leq 16$ and $0 \leq a \leq 3$.

7. Water-soluble thickening polymers according to claim 1, wherein their hydrophobic, non-olymeric radicals are groups

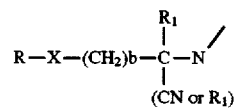

in which R is an organic hydrophobic radical selected from the group consisting of alkyl or cycloalkyl hydrocarbon aliphatic groups containing from 4 to 20 carbons, aromatic polynuclear groups, alkylaryl groups and polyalkylene oxide groups where the alkylene is propylene or a higher homologue, with at least one alkylene unit per hydrophobic section, X denotes either a direct bond or a divalent group, optionally CO, COO, OCO or SO$_2$, an oxygen atom or a sulphur atom; b is an integer ranging from 0 to 11; and R$_1$ denotes an alkyl group containing from 1 to 4 carbon atoms.

8. Water-soluble thickening polymers according to claim 1, wherein their hydrophobic, non-polymeric radicals are groups

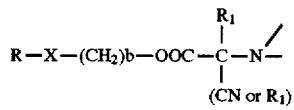

in which R is an organic hydrophobic radical selected from the group consisting of alkyl or cycloalkyl hydrocarbon aliphatic groups containing from 4 to 20 carbons, aromatic polynuclear groups, alkylaryl groups and polyalkylene oxide groups where the alkylene is propylene or a higher homologue, with at least one alkylene unit per hydrophobic segment, X denotes either a direct bond or a divalent group, optionally CO, COO, OCO or SO$_2$, an oxygen atom or a sulphur atom; b is an integer ranging from 0 to 11; and R$_1$ denotes an alkyl group containing from 1 to 4 carbon atoms.

9. Water-soluble thickening polymers according to claim 1, wherein their hydrophobic, non-polymeric radicals are groups

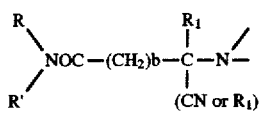

in which R is an organic hydrophobic radical selected from the group consisting of alkyl or cycloalkyl hydrocarbon aliphatic groups containing from 4 to 20 carbons, aromatic polynuclear groups, alkylaryl groups and polyalkylene oxide groups where the alkylene is propylene or a higher homologue, with at least one alkylene unit per hydrophobic segment, X denotes either a direct bond or a divalent group, optionally CO, COO, OCO or $SO_2$, an oxygen atom or a sulphur atom; b is an integer ranging from 0 to 11; $R_1$ denotes an alkyl group containing from 1 to 4 carbon atoms; and where R' is R or a hydrogen atom.

10. Water-soluble thickening polymers according to claim 1, wherein N-substituted compounds are 2-acrylamido-2-methylpropanesulphonic acid, N-(dimethylamino) methylacrylamide, N-(trimethylammonium) methylacrylamide chloride.

11. Water-soluble thickening polymers according to claim 1, wherein the amino alkyl esters are N,N-dimethylaminoethyl acrylate, and N-vinyl-2-pyrrolidone.

* * * * *